United States Patent
King et al.

(10) Patent No.: US 8,961,939 B2
(45) Date of Patent: Feb. 24, 2015

(54) COMPOSITIONS AND RELATED METHODS FOR ORAL WELLNESS

(75) Inventors: Janice Lou King, Kansas City, MO (US); Dale Leland Winetroub, Kansas City, MO (US)

(73) Assignee: NowSystem, Inc., Kansas City, KS (US)

( * ) Notice: Subject to any disclaimer, the term of this patent is extended or adjusted under 35 U.S.C. 154(b) by 235 days.

(21) Appl. No.: 13/405,177

(22) Filed: Feb. 24, 2012

(65) Prior Publication Data

US 2013/0224129 A1    Aug. 29, 2013

(51) Int. Cl.
*A61Q 11/00* (2006.01)
*A61K 36/00* (2006.01)
*A61K 8/22* (2006.01)

(52) U.S. Cl.
USPC ............. 424/49; 424/53; 424/58; 424/485; 424/401; 514/901

(58) Field of Classification Search
USPC .................. 424/49, 53, 58, 485; 514/901
See application file for complete search history.

(56) References Cited

U.S. PATENT DOCUMENTS

2007/0166238 A1*   7/2007   Duggan et al. .................. 424/46

OTHER PUBLICATIONS

Healing Vibes, Organic Wheat Grass Powder—New Zealand, http://www.healingvibes.com/products/foods/wheatgrass.html, May 2008, pp. 1-3.*
Nowsystem, ELEVA Naturals Products, http://www/hotfrog.com/Companies/Nowsystem/EL%C3%89VA-Naturals-Products-758086, Nov. 25, 2011, p. 1.*
Green Planet Company, PerioPaste—Natural Toothpaste, http://www.greenplanetcompany.net/periopaste.html, May 2009, pp. 1-2.*

* cited by examiner

*Primary Examiner* — Lezah Roberts
(74) *Attorney, Agent, or Firm* — Kelley Schnieders; Patrick C. Woolley; Polsinelli PC

(57) ABSTRACT

Disclosed are compositions, apparatus, and related methods and systems for oral health care.

5 Claims, No Drawings dis-
COMPOSITIONS AND RELATED METHODS FOR ORAL WELLNESS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of Invention

The present application is within the field of compositions and related methods or systems of health and oral care.

2. Background of the Invention

Poor oral health is thought to contribute to a person's declining general health. For instance, the U.S. Surgeon General has reported findings of possible associations between poor oral health and diabetes, heart and lung diseases, strokes, low birth weight and premature births. Surgeon General's Report on Oral Health, May 2000. Accordingly, there is a need for compositions and related methods or systems of oral health care.

A major focus of correcting poor oral health has heretofore been oral hygiene and compositions and related methods have long been known and used for this purpose. Typically, such compositions are usually applied in some manner to the soft and hard tissues of an oral cavity and suitably contain active ingredients for cleaning and whitening teeth, medicinally treating ailments in the oral cavity soft tissue (e.g., gums), and killing disease or halitosis causing bacteria or fungi occupying the oral cavity. See, e.g., U.S. Pat. No. 0,030,834 (issued Dec. 4, 1860) (col. 2: 1-17 disclosing a fungicidal composition for cleaning and whitening teeth, preventing tooth decay, tooth-ache pain relief, gum treatments, and bad-breath removal); U.S. Pat. No. 0,050,110 (issued Nov. 26, 1865) (col. 1: 9-15 disclosing a scented composition for cleaning teeth and preventing tooth decay); U.S. Pat. No. 0,069,393 (issued Oct. 1, 1867), U.S. Pat. No. 0,085,166 (issued Dec. 22, 1868), U.S. Pat. No. 0,111,821 (issued Feb. 14, 1871), U.S. Pat. No. 0,196,275 (issued Oct. 16, 1877), U.S. Pat. No. 0,284,751 (issued Sep. 11, 1883), U.S. Pat. No. 1,467,455 (issued Sep. 11, 1923), U.S. Pat. No. 1,527,523 (issued Feb. 24, 1925), U.S. Pat. No. 4,407,788 (issued Oct. 4, 1983), U.S. Pat. No. 4,153,680 (issued May 8, 1979), U.S. Pat. No. 4,153,680 (issued Dec. 1, 1981), U.S. Pat. No. 5,939,050 (issued Aug. 17, 1999) (disclosing compositions for cleaning components of the oral cavity); U.S. Pat. No. 0,108,845 (issued Nov. 1, 1870) (col. 1: 1-9 disclosing a composition "for cleansing and preserving teeth, healing diseased gums, tightening loose teeth, preventing toothache, removing canker, and restoring vitiated breath and taste"); U.S. Pat. No. 0,118,813 (Sep. 12, 1871) (col. 1:9-11 disclosing an antiseptic composition for preserving and beautifying teeth); U.S. Pat. No. 0,129,469 (issued Jul. 16, 1872) (col. 2:13-15 disclosing a composition for "cleaning teeth, purifying the mouth, and sweetening the breath"); U.S. Pat. No. 0,137,542 (issued Apr. 8, 1873) and U.S. Pat. No. 0,428,033 (issued May 13, 1890) (disclosing a mouthwash for freshening breath and treating bleeding or swollen gums); U.S. Pat. No. 1,073,725 (Sep. 23, 1913) (col. 1:8-14 disclosing a composition for strengthening the gums, cleansing the teeth and purifying the breath); U.S. Pat. No. 1,523,840 (issued Jan. 20, 1925) (col. 1:12-19 disclosing a composition "which not only cleans and polishes the teeth, but absorbs impurities, massages the gums, stimulating the soft tissues and increasing the blood supply, and finally has a pleasing and appropriate flavor); U.S. Pat. No. 1,527,523 (issued Feb. 24, 1925); U.S. Pat. No. 1,551,638 (issued Sep. 1, 1925) (disclosing a composition for treating oral diseases); U.S. Pat. No. 1,558,160 (issued Oct. 20, 1925) (col. 1:8-12 disclosing a composition that will clean, stimulate and invigorate the soft tissues composing the oral cavity); U.S. Pat. No. 1,916,403 (issued Jul. 4, 1933); U.S. Pat. No. 2,697,060 (issued Dec. 14, 1954) (disclosing a composition for the treatment of inflamed gums (i.e., gingivitis)); U.S. Pat. No. 2,955,985 (issued Oct. 11, 1960) (disclosing a composition for strengthening the gums); and, U.S. Pat. No. 3,124,506 (issued Mar. 10 1964) (col. 1:17-31 disclosing compositions featuring "tartar removing agent, antienzyme, and sanitizer"); U.S. Pat. No. 3,137,632 (issued Jan. 16, 1964) (disclosing compositions for treating and curing wounds and gum disease); U.S. Pat. No. 5,122,365 (issued Jun. 16, 1992), U.S. Pat. No. 5,171,564 (issued Dec. 15, 1992), U.S. Pat. No. 5,858,332 (issued Jan. 12, 1999) (disclosing teeth whitening); U.S. Pat. No. 3,956,478 (issued May 11, 1976); U.S. Pat. No. 4,242,323 (issued Dec. 30, 1980) (disclosing plaque inhibiting compositions); U.S. Pub. Pat. App. No. US20080031831 (published Feb. 2, 2008) (disclosing an anti-calculus composition comprised of an antiseptic and anti-inflammatory); US20050201953 (published Aug. 15, 2005) (disclosing bacteria killing compositions for freshening breath and disease prevention). However, correcting poor oral health and oral illness requires, among other things and in addition to oral hygiene, the systematic removal of toxic loads provided to the oral cavity, delivery of nutrients to the oral cavity, and rejuvenation of the oral cavity. For this reason, known oral hygiene compositions and related methods fall short of adequately addressing the need for compositions and related methods or systems of oral health care.

Removal of toxic loads is critical in terms of oral health and oral wellness because toxins (e.g., such as Propylene Glycol, Sodium Lauryl Sulfate, Polyethylene, and the like) have been linked to various bodily ailments (e.g., joint pain, skin irritations, hair loss, depression, diarrhea, mouth sores, and cold like symptoms). In an effort to remove toxic loads provided to the oral cavity, known oral hygiene compositions have been comprised of non-toxic ingredients. See e.g., U.S. Pat. No. 0,030,834 (disclosing a composition that does not contain "poisonous ingredients . . . so that it can be used with perfect safety and without danger."). However, merely omitting toxic ingredients from dentifrice compositions does not address the need for active removal of toxic loads from the oral cavity. Others have proposed composing dentifrices of natural ingredients including a fraction containing anti-oxidant rich plant extracts. See U.S. Pat. No. 7,083,779 (issued Aug. 1, 2006). However, even while possessing anti-oxidants, known compositions have failed to provide nutrients to the oral cavity. For these reasons, a need still exists for compositions and related methods or systems of oral health care.

Oral nutrition is also important for oral health and oral wellness. Nutrients have previously been provided to the oral cavity via the use of an oral hygiene composition including a nutrient rich fraction wherein nutrients therefrom are absorbed by the soft-tissue components of the inner oral cavity. See U.S. Pat. No. 1,916,403 (issued Jul. 4, 1933) (col. 1:37-2:56 (disclosing the addition of citrus plant pieces to a dentifrice composition so that Vitamin A, B, and C can be absorbed through the gums while the user is brushing his/her teeth); see also U.S. Pat. No. 6,207,137 (issued Mar. 27, 2001) (disclosing a dentifrice with an active component having Vitamin C in an amount of 10 and 25 weight percent) and U.S. Pat. No. 5,294,434 (issued Mar. 15, 1994) (disclosing use of aloe vera and chlorophyll in an oral hygiene composition to stimulate tissue cell growth). Although absorption of nutrients through the soft-tissues of the oral cavity is suitable for nutrient delivery in terms of oral health care, the known compositions employing such a delivery mechanism can be improved in terms of the types and concentrations of nutrient rich ingredients within a composition and methods or systems of for delivering the composition. More specifically, the recited patents (U.S. Pat. Nos. 1,916,403, 6,207,137 and, 5,294,434) disclose absorption of nutrients from citrus fruit, aloe vera or vitamin powder composing pastes/gels that are contacted to the gums while brushing teeth, yet: other types of ingredients may be more nutrient rich while simultaneously possessing better oral hygiene characteristics; and, other compositions and modes of soft-tissue contact may be more conducive to nutrient absorption. Additionally, the known compositions disclosing nutrient absorption do not feature active removal of toxic loads provided to the oral cavity. For these reason, a need still exists for compositions and related methods or systems of health and oral care.

In addition to the above identified inadequacies of known oral hygiene compositions, known methods and systems for the application of compositions to the oral cavity are also inadequate in terms of treating and preventing poor oral health. Once again, known methods and systems for the application of compositions to the oral cavity focus on promoting oral hygiene or other issues instead of treating poor oral health. See U.S. Pat. No. 0,030,834 (disclosing every day application of a oral hygiene cream), U.S. Pat. No. 0,069,393 (disclosing a lozenge for oral hygiene), U.S. Pat. No. 5,098,297 (issued Mar. 24, 1992) (disclosing an apparatus for placing desensitizer on a tooth), U.S. Pat. No. 5,616,187 (issued Mar. 18, 1997) (disclosing an portable apparatus for placing teeth whitener on a tooth), U.S. Pat. No. 4,023,712 (issued May 17, 1977) (disclosing a portable breath spray), and U.S. Pat. No. 7,309,185 (issued Dec. 18, 2007) (disclosing a portable toothbrush with self contained toothpaste); see also U.S. Pub Pat. App. Nos. 20050158252 (published Jul. 21, 2005) (disclosing an oral hygiene solution that is administered in drinking water), 20070292372 (published Dec. 20, 2007) and 20070292367 (published Dec. 20, 2007) (disclosing a method for regular application of oral compositions), and 20090202452 (published Aug. 13, 2009) (disclosing daily and monthly applications of different types of oral hygiene compositions). The known oral hygiene compositions fail to account for harmful bacteria growing in the oral cavity twenty-four hours a day, toxic loads being periodically provided to the oral cavity throughout the day, and multiple daily doses of nutrients being preferable for rebuilding healthy oral cavity cells and immune system support. Also, many of the available compositions and related methods have been expensive and can only be acquired and practiced at a dentist's office. For these reasons, there is a need for compositions and related methods/systems that provide all-day oral health care and that are readily available to the general public.

Known dentifrice compositions and oral medications have not yet been entirely satisfactory for treating poor oral health, particularly in circumstances where oral tissue has become extremely sensitive. For instance, oral diseases or conditions such as dry mouth (Xerostomia) or thrush (candidiasis oral), which are frequently associated with the use of prescription and over-the-counter drugs (There are over 400 prescription and over the counter drugs that cause dry mouth symptoms (e.g., Xerostomia is common due to radiation or chemotherapy treatments)), often result in oral tissue that is too sensitive for topical treatment by effective dentifrice or medicated treatments (extreme cases of thrush sometimes result in oral tissue that is so sensitive that the infected person would rather starve or dehydrate than contact the oral cavity with food or water). Accordingly, a need exists for natural compositions and related methods/systems for treating sensitive oral tissue.

Yet still, known dentifrice compositions and oral medications have not been entirely satisfactory in circumstances where subgingival oral health is poor. For example, periodontal (gum) disease has, in the past, been treated by scaling and root planing (e.g., scraping the disease causing bacteria from between the teeth and gums of the patient) plus application of medications such as chlorhexidine and Arestin® Minocycline HC1 (Arestin® is a powder-like antibiotic substance that is deposited between the teeth and gums after scaling and planing). Arestin® has not been entirely satisfactory for treating subgingival oral health because, among other things: use of Arestin®, a tetracycline class drug, may cause permanent discoloration of the teeth and gums, and therefore, should not be used in children or in pregnant or nursing women; hypersensitivity reactions (e.g., anaphaylaxis, angioneurotic edema, urticaria, rash, swelling of the face, pruritus, headache, infection, flu syndrome, and pain have been reported with use of Arestin®); minocycline may cause upset stomach, diarrhea, dizziness, unsteadiness, drowsiness, mouth sores, and vomiting; Arestin® is not a naturally-occurring antibiotic, but is rather synthesized semi-synthetically from natural tetracycline antibiotics and comprised of potentially toxic ingredients; and, as an antibiotic, it does not promote growth and healing of damaged oral tissue. The effects of Chlorhexidine gluconate on periodontitis have not been entirely determined. However, it is thought that Chorhexidine is not entirely satisfactory for treating oral health because: an increase in supragingival calculus has been noted in clinical testing; Chlorhexidine's effectiveness and safety have not been established in children under the age of 18; Chlorhexidine gluconate often causes staining of oral surfaces, including tooth surfaces, restorations, and the dorsum on the tongue; chlorhexidine may cause alterations in taste perception, which in some instances result in permanent taste alteration; chlorhexidine may have the side effects of burning sensations of the oral soft tissues, soreness and dryness of the oral tissues, and desquamative lesions and ulcerations of the gingival mucosa; and, Chlorhexidine has a strong and unpleasant taste. Thus, there remains a need for natural compositions and related methods/systems for treating subgingival oral health conditions in patients of all ages and stages of overall health and wellness.

SUMMARY OF THE INVENTION

It is an object of the present application to disclose non-toxic and nutrient rich compositions and related methods or systems of health and oral care in addition to oral hygiene applications. More specifically, it is an object of the present invention to provide compositions and related systems and methods for treating poor oral health, including the promotion of oral hygiene, active toxic load reduction, rejuvenation of the oral cavity, and the provision of nutrients to the oral cavity. It is a further object of the present disclosure to provide compositions that may be applied to the oral cavity in a number of different manners. It is another object of the present application to disclose compositions and methods for all-day oral health care. It is yet still an object of the present invention to provide compositions and related methods that are readily available and inexpensive. It is yet still an object of this disclosure to provide compositions and related methods for controlling mouth infections and bacteria (e.g., periodontal disease) via providing pain reduction, inflammation reduction, odor control (e.g., via killing odor causing bacteria such as sulfur producing anaerobic bacteria), and, promotion of damaged tissue repair. It is yet still another object of the present disclosure to provide compositions and related methods which are safe for children, pregnant and nursing women, the elderly, and special-care individuals.

A first preferable embodiment of this disclosure for implementing the recited objectives may be a non-toxic rinse, gel, toothpaste, or serum composition for topical or subgingival application to the inner components of an oral cavity (e.g., teeth, gums, throat, and/or tongue). The rinse composition may be a mouth rinse or a mouth spray for topical application to the oral cavity. The gel composition may be for topical treatment of the oral cavity or for toothpaste. The serum composition may be used for treating supragingival or subgingival oral conditions. In one embodiment, the rinse composition may comprise: Distilled Water; Organic Whole Leaf wheat grass; Xylitol from Birch Wood; Certified Organic Vegetable Glycerin; Organic Aloe Vera Juice; Carbamide Peroxide; Sweet Almond Oil; Pure Peppermint Oil; and Xanthan Gum. The toothpaste composition may comprise: Organic Whole Leaf wheat grass; Xylitol from Birch Wood; Certified Organic Vegetable Glycerin; Organic Aloe Vera Powder; Sweet Almond Oil; Pure Peppermint Oil; and, Xanthan Gum. For the treatment of sensitive oral tissue or young children (aged between 2 and 12 years), the gel and rinse composition may be made according to gentle care formulations. The serum composition may comprise: Organic Aloe Vera Juice; Xanthan Gum; Organic Whole Leaf wheat grass; Carbamide Peroxide; Sweet Almond Oil; Pure Peppermint Oil; and Certified Organic Vegetable Glycerin. In any composition, nutrients may be delivered to a user via absorption through the soft tissue of the mouth, bacteria may be controlled or killed, oral wounds/conditions may be treated, breath may be freshened, and teeth may be whitened.

Other objectives and desires may become apparent to one of skill in the art after reading the below disclosure.

BRIEF DESCRIPTION OF THE FIGURES

Not applicable.

DETAILED DESCRIPTION OF PREFERRED EMBODIMENTS

In general, the present application discloses non-toxic compositions that are applied to the internal components of the oral cavity for oral health care. The compositions may be a rinse, an oral care gel, a toothpaste, or a supragingival or subgingival serum. The compositions, among other things, suitably kill harmful pathogens and halitosis causing bacteria or fungus, contain antioxidants for removing toxins, strengthen and whiten teeth, moisturize oral tissue, rejuvenate the oral cavity, and deliver nutrients to the oral cavity to rebuild healthy cells and support the immune system. Additionally, the present application discloses methods of making the compositions and methods of using the compositions. Finally, the present application discloses a system for facilitating good oral health and oral wellness.

A. Compositions

1. Rinse Compositions

The rinse may be comprised of: distilled water; organic whole leaf wheat grass; xylitol from Birch wood; certified organic vegetable glycerin; organic aloe vera juice; carbamide peroxide; sweet almond oil; pure peppermint oil; and xanthan gum. The disclosed composition has been preferable for ordinary oral health care when the component ingredients are featured in the following amounts: 5.98 gallons of distilled water; 2,395.00 grams of Xylitol; 119.70 grams of Peppermint Oil; 981.90 grams of Vegetable Glycerin; 910.10 grams of Aloe Vera Juice; 718.5 grams of Carbamide Peroxide; 311.30 grams of Sweet Almond Oil; 119.70 grams of wheat grass powder; and, 12.90 grams of Xanthan Gum.

The amounts of the component ingredients within the composition may suitably be manipulated to adjust the oral health care properties of the composition. For instance, in another embodiment, the disclosed composition has also been preferable for treatment of sensitive oral tissue or the oral tissue of young children (ages less than twelve years) when the amount of carbamide peroxide is reduced to zero while the remaining component ingredients are featured in the following amounts: 3.12 gallons of distilled water; 1,197.99 grams of xylitol; 47.92 grams of peppermint oil; 491.18 grams of vegetable glycerin; 455.24 grams of aloe vera juice; 155.74 grams of sweet almond oil; 59.90 grams of wheat grass powder; and, 11.98 grams of xanthan gum. For another instance, the tooth whitening properties of the mouth wash may be preferably enhanced when the component ingredients are featured in the following amounts: 12,093.00 grams of distilled water; 315.00 grams of xylitol; 20.00 grams of peppermint oil; 880.00 grams of vegetable glycerin; 130.00 grams of aloe vera juice; 1,500.00 grams of carbamide peroxide; 150.00 grams of Sweet Almond Oil; 20.00 grams of wheat grass powder; and, 12.00 grams of xanthan gum. For another instance, the composition may be more concentrated for professional oral health care by including the component ingredients in the following amounts: 4.73 gallons of distilled water; 2,395.00 grams of xylitol; 119.70 grams of peppermint oil; 981.9 grams of vegetable glycerin; 910.10 grams of aloe vera juice; 718.50 grams of carbamide peroxide; 311.30 grams of sweet almond oil; 119.70 grams of wheat grass powder; and, 12.90 grams of xanthan gum. In yet another embodiment, the disclosed composition has also been preferable for professional treatment of sensitive oral tissue or young children when the amount of carbamide peroxide is reduced to zero while the remaining component ingredients are featured in the following amounts: 2.37 gallons of distilled water; 1,197.99 grams of xylitol; 47.92 grams of peppermint oil; 491.18 grams of vegetable glycerin; 455.24 grams of aloe vera juice; 155.74 grams of sweet almond oil; 59.90 grams of wheat grass powder; and, 11.98 grams of xanthan gum. The above recited preferable amounts of each ingredient are summarized by Table 1.

TABLE 1

Compositions for the mouth rinses

| Ingredient | Amount | |
|---|---|---|
| Ordinary Oral Health Care | | |
| distilled water | 5.98 | gal. |
| xylitol | 2,395.00 | gm |
| peppermint oil | 119.70 | gm |
| vegetable glycerin | 981.90 | gm |
| aloe vera juice | 910.10 | gm |
| carbamide peroxide | 718.50 | gm |
| sweet almond oil | 311.30 | gm |
| wheat grass powder | 119.70 | gm |
| xanthan gum | 12.90 | gm |
| Sensitive Tissue Ordinary Oral Health Care | | |

TABLE 1-continued

Compositions for the mouth rinses

| Ingredient | Amount | |
|---|---:|---|
| distilled water | 3.12 | gal. |
| xylitol | 1,197.99 | gm |
| peppermint oil | 47.92 | gm |
| vegetable glycerin | 491.18 | gm |
| aloe vera juice | 455.24 | gm |
| sweet almond oil | 155.74 | gm |
| wheat grass powder | 59.90 | gm |
| xanthan gum | 11.98 | gm |
| Teeth whitening | | |
| distilled water | 12,093.00 | gm |
| xylitol | 315.00 | gm |
| peppermint oil | 20.00 | gm |
| vegetable glycerin | 880.00 | gm |
| aloe vera juice | 130.00 | gm |
| carbamide peroxide | 1,500 | gm |
| sweet almond oil | 150.00 | gm |
| wheat grass powder | 20.00 | gm |
| xanthan gum | 12.00 | gm |
| Professional Oral Health Care | | |
| distilled water | 4.73 | gal. |
| xylitol | 2,395.00 | gm |
| peppermint oil | 119.70 | gm |
| vegetable glycerin | 981.90 | gm |
| aloe vera juice | 910.10 | gm |
| carbamide peroxide | 718.50 | gm |
| sweet almond oil | 311.30 | gm |
| wheat grass powder | 119.70 | gm |
| xanthan gum | 12.90 | gm |
| Sensitive Tissue Professional Oral Health Care | | |
| distilled water | 2.37 | gal. |
| xylitol | 1,197.99 | gm |
| peppermint oil | 47.92 | gm |
| vegetable glycerin | 491.18 | gm |
| aloe vera juice | 455.24 | gm |
| sweet almond oil | 155.74 | gm |
| wheat grass powder | 59.90 | gm |
| xanthan gum | 11.98 | gm |

Those of skill in the art will know well the manner by which the above identified ingredients can be obtained or produced. This said: distilled water may be created by condensing steam; organic whole leaf wheat grass powder may be purchased from Pines International (milled to less than 100 mesh by Union Process, Inc.); xylitol from Birch wood may be purchased from Danisco USA, Inc.; pure peppermint oil may be purchased from ASN/Nutritiongeeks.com; carbamide peroxide may be purchased from American Intl Chemical, Inc.; organic aloe vera juice and powder, certified organic vegetable glycerin, and sweet almond oil may be purchased from Jedwards Intl Inc.; and xanthan gum may be purchased from The Great American Spice Company, Inc.

A 7.25 gallon batch of the rinse composition for ordinary oral health care may be prepared by: first, mixing 119.70 grams of wheat grass powder with approximately 0.589 gallons of distilled water until the wheat grass powder hydrates thoroughly (approximately 30 minutes); second, slowly mixing 12.90 grams of xanthan gum and approximately 0.897 gallons of distilled water until no clumps of xanthan gum are present (the mixture should preferably be allowed to thicken for one to two hours); third, mixing 718.50 grams of carbamide peroxide, approximately 4.485 gallons of distilled water, and 910.10 grams of aloe vera juice until the carbamide peroxide is thoroughly dissolved; fourth, mixing 2,395.00 grams of xylitol with the resultant mixture from the third step until the xylitol is thoroughly dissolved; fifth, mixing the mixtures of the first, second, and fourth steps together; sixth, mixing 981.90 grams of vegetable glycerin, 311.30 grams of sweet almond oil, and 119.70 grams of peppermint oil; and, seventh, mixing the mixtures of the fifth and sixth steps at high speed until homogenous.

A 3.75 gallon batch of the rinse composition for ordinary oral health care for sensitive tissue or children may be prepared by: first, mixing 59.90 grams of wheat grass powder with approximately 0.312 gallons of distilled water until the wheat grass powder hydrates thoroughly (approximately 30 minutes); second, slowly mixing 11.98 grams of xanthan gum and approximately 0.468 gallons of distilled water until no clumps of xanthan gum are present (the mixture should preferably be allowed to thicken for one to two hours); third, mixing approximately 2.34 gallons of distilled water and 455.24 grams of aloe vera juice; fourth, mixing 1,197.99 grams of xylitol with the resultant mixture from the third step until the xylitol is thoroughly dissolved; fifth, mixing the mixtures of the first, second, and fourth steps together; sixth, mixing 491.18 grams of vegetable glycerin, 155.74 grams of sweet almond oil, and 47.92 grams of peppermint oil; and, seventh, mixing the mixtures of the fifth and sixth steps at high speed until homogenous.

A 15,120.00 gram batch of the rinse composition for teeth whitening may be prepared by: first, mixing 20.00 grams of wheat grass powder with approximately 1,209.30 grams of distilled water until the wheat grass powder hydrates thoroughly (approximately 30 minutes); second, slowly mixing 12.00 grams of xanthan gum and approximately 1,813.95 grams of distilled water until no clumps of xanthan gum are present (the mixture should preferably be allowed to thicken for one to two hours); third, mixing 1,500.00 grams of carbamide peroxide, approximately 9069.75 grams of distilled water, and 130.00 grams of aloe vera juice until the carbamide peroxide is thoroughly dissolved; fourth, mixing 315.00 grams of xylitol with the resultant mixture from the third step until the xylitol is thoroughly dissolved; fifth, mixing the mixtures of the first, second, and fourth steps together; sixth, mixing 880.00 grams of vegetable glycerin, 150.00 grams of sweet almond oil, and 20.00 grams of peppermint oil; and, seventh, mixing the mixtures of the fifth and sixth steps at high speed until homogenous.

A 6.00 gallon batch of the rinse composition for professional oral health care may be prepared by: first, mixing 119.70 grams of wheat grass powder with approximately 0.473 gallons of distilled water until the wheat grass powder hydrates thoroughly (approximately 30 minutes); second, slowly mixing 12.90 grams of xanthan gum and approximately 0.7095 gallons of distilled water until no clumps of xanthan gum are present (the mixture should preferably be allowed to thicken for one to two hours); third, mixing 718.50 grams of carbamide peroxide, approximately 3.5475 gallons of distilled water, and 910.10 grams of aloe vera juice until the carbamide peroxide is thoroughly dissolved; fourth, mixing 2,395.00 grams of xylitol with the resultant mixture from the third step until the xylitol is thoroughly dissolved; fifth, mixing the mixtures of the first, second, and fourth steps together; sixth, mixing 981.90 grams of vegetable glycerin, 311.30 grams of sweet almond oil, and 119.70 grams of peppermint oil; and, seventh, mixing the mixtures of the fifth and sixth steps at high speed until homogenous.

A 3.00 gallon batch of the rinse composition for professional oral health care for sensitive tissue or children may be prepared by: first, mixing 59.90 grams of wheat grass powder with approximately 0.237 gallons of distilled water until the wheat grass powder hydrates thoroughly (approximately 30 minutes); second, slowly mixing 11.98 grams of xanthan gum and approximately 0.3555 gallons of distilled water until no clumps of xanthan gum are present (the mixture should preferably be allowed to thicken for one to two hours); third, mixing approximately 1.7775 gallons of distilled water and 455.24 grams of aloe vera juice; fourth, mixing 1,197.99 grams of xylitol with the resultant mixture from the third step until the xylitol is thoroughly dissolved; fifth, mixing the mixtures of the first, second, and fourth steps together; sixth, mixing 491.18 grams of vegetable glycerin, 155.74 grams of sweet almond oil, and 47.92 grams of peppermint oil; and, seventh, mixing the mixtures of the fifth and sixth steps at high speed until homogenous. Those skilled in the art will appreciate how this formulation(s) may be scaled up or down to accommodate different batch sizes.

2. Gel Compositions

The gel composition may comprise: organic whole leaf wheat grass; xylitol from Birch wood; certified organic vegetable glycerin; organic aloe vera juice; sweet almond oil; pure peppermint oil; and, xanthan gum. The disclosed composition has been most preferable for oral health care when the component ingredients are featured in the following amounts: 4.00 grams of organic whole leaf wheat grass powder; 200.00 grams of xylitol from Birch wood; 200.00 grams of certified organic vegetable glycerin; 200.00 grams of organic aloe vera juice; 50.00 grams of sweet almond oil; 4.00 grams of pure peppermint oil; and, 8.00 grams of xanthan gum. The above preferable compositions are summarized by Table 2.

TABLE 2

Compositions for the oral care gel

| Ingredient | amount | |
|---|---|---|
| wheat grass | 4.00 | gm |
| xylitol | 200.00 | gm |
| vegetable glycerin | 200.00 | gm |
| aloe vera juice | 200.00 | gm |
| almond oil | 50.00 | gm |
| peppermint oil | 4.00 | gm |
| xanthan gum | 8.00 | gm |

A 666.00 gram batch of the oral care gel may be prepared by: first, mixing 20.00 grams of aloe vera juice with 4.00 grams of wheat grass powder until the wheat grass powder is thoroughly hydrated (approximately 30 minutes); second, mixing 80.00 grams of aloe vera juice with 8.00 grams of xanthan gum until there are no clumps of xanthan gum present (the mixture should preferably be allowed to thicken for one to two hours); third, mixing 100.00 grams of aloe vera juice with 200.00 grams of xylitol until the xylitol is dissolved; fourth, mixing the mixtures of the first through third steps; fifth, mixing 200.00 grams of vegetable glycerin, 50.00 grams of sweet almond oil, and 4.00 grams of peppermint oil; and, sixth mixing the mixtures of the fourth and fifth steps. Those skilled in the art will appreciate how this formulation(s) may be scaled up or down to accommodate different batch sizes.

The toothpaste gel composition may also comprise: distilled water; organic whole leaf wheat grass; xylitol from Birch wood; certified organic vegetable glycerin; organic aloe vera powder; carbamide peroxide; sweet almond oil; pure peppermint oil; and xanthan gum. The disclosed composition has been preferable for ordinary oral health care when the component ingredients are featured in the following amounts: 280.00 grams of distilled water; 554.00 grams of xylitol; 4.00 grams of peppermint oil; 168.00 grams of vegetable glycerin; 0.50 grams of aloe vera powder; 100.00 grams of carbamide peroxide; 44.00 grams of sweet almond oil; 4.00 grams of wheat grass powder; and, 8.00 grams of xanthan gum.

As with the components of the rinse composition, amounts of the component ingredients within the gel composition may suitably be manipulated to adjust the oral health care properties of the composition. For instance, in another embodiment, the disclosed composition has also been preferable for treatment of sensitive oral tissue when the amount of carbamide peroxide is reduced to zero while the remaining component ingredients are featured in the following amounts: 280.00 grams of distilled water; 554.00 grams of xylitol; 4.00 grams of peppermint oil; 168.00 grams of vegetable glycerin; 0.50 grams of aloe vera powder; 44.00 grams of sweet almond oil; 4.00 grams of wheat grass powder; and, 8.00 grams of xanthan gum. In yet another embodiment, the disclosed composition has also been preferable for treatment of the oral tissue of young children (ages less than twelve years) when component ingredients plus orange oil are featured in the following amounts: 280.00 grams of distilled water; 554.00 grams of xylitol; 4.00 grams of peppermint oil; 168.00 grams of vegetable glycerin; 0.50 grams of aloe vera powder; 44.00 grams of sweet almond oil; 4.00 grams of wheat grass powder; 8.00 grams of xanthan gum; and 20.00 grams of pure orange oil. The above recited preferable compositions are summarized by Table 3.

TABLE 3

Compositions for the gel composition

| Ingredient | amount | |
|---|---|---|
| Retail Composition | | |
| distilled water | 280.00 | gm |
| xylitol | 554.00 | gm |
| peppermint oil | 4.00 | gm |
| vegetable glycerin | 168.00 | gm |
| aloe vera powder | 0.50 | gm |
| carbamide peroxide | 100 | gm |
| sweet almond oil | 44.00 | gm |
| wheat grass powder | 4.00 | gm |
| xanthan gum | 8.00 | gm |
| Sensitive Oral Tissue Composition | | |
| distilled water | 280.00 | gm |
| xylitol | 554.00 | gm |
| peppermint oil | 4.00 | gm |
| vegetable glycerin | 168.00 | gm |
| aloe vera powder | 0.50 | gm |
| sweet almond oil | 44.00 | gm |
| wheat grass powder | 4.00 | gm |
| xanthan gum | 8.00 | gm |
| Gel Composition for Children | | |
| distilled water | 280.00 | gm |
| xylitol | 554.00 | gm |
| peppermint oil | 4.00 | gm |
| vegetable glycerin | 168.00 | gm |
| aloe vera powder | 0.50 | gm |
| sweet almond oil | 44.00 | gm |
| wheat grass powder | 4.00 | gm |
| xanthan gum | 8.00 | gm |
| Orange Oil | 20.00 | gm |

A 1,132.00 gram batch of the toothpaste gel composition for ordinary oral health care may be prepared by: first, mixing 200.00 grams of distilled water, 100.00 grams of carbamide peroxide, and 554.00 grams of xylitol until the carbamide peroxide and xylitol are dissolved or thoroughly hydrated by the water (approximately 30 minutes); second, slowly mixing 80.00 grams of water with 8.00 grams of xanthan gum until no clumps of xanthan gum are present (the mixture should preferably be allowed to thicken for one to two hours); third, mixing 0.5 grams of aloe vera powder with 4.00 grams of wheat grass powder; fourth, mixing 168.00 grams of vegetable glycerin, 44.00 grams of sweet almond oil, 4.00 grams of peppermint oil, and the resultant mixture from the third step; fifth, mixing the mixtures from the first and fourth steps at high speed until homogenous; and sixth, mixing the mixtures from the second and fifth steps at high speed until homogenous.

A 1,032.00 gram batch of the toothpaste gel for oral health care for sensitive mouth tissue may be prepared by: first, mixing 200.00 grams of distilled water and 554.00 grams of xylitol until the xylitol is dissolved or thoroughly hydrated by the water (approximately 30 minutes); second, slowly mixing 80.00 grams of water with 8.00 grams of xanthan gum until no clumps of xanthan gum are present (the mixture should preferably be allowed to thicken for one to two hours); third, mixing 0.5 grams of aloe vera powder with 4.00 grams of wheat grass powder; fourth, mixing 168.00 grams of vegetable glycerin, 44.00 grams of sweet almond oil, 4.00 grams of peppermint oil, and the resultant mixture from the third step until no clumps of the mixture from the third step are present; fifth, mixing the mixtures from the first and fourth steps at high speed until homogenous; and sixth, mixing the mixtures from the second and fifth steps at high speed until homogenous.

A 1,052.00 gram batch of the toothpaste gel for oral health care for sensitive mouth tissue may be prepared by: first, mixing 200.00 grams of distilled water and 554.00 grams of xylitol until the xylitol is dissolved or thoroughly hydrated by the water (approximately 30 minutes); second, slowly mixing 80.00 grams of water with 8.00 grams of xanthan gum until no clumps of xanthan gum are present (the mixture should preferably be allowed to thicken for one to two hours); third, mixing 0.5 grams of aloe vera powder with 4.00 grams of wheat grass powder; fourth, mixing 168.00 grams of vegetable glycerin, 44.00 grams of sweet almond oil, 4.00 grams of peppermint oil, 20.00 grams of orange oil, and the resultant mixture from the third step until no clumps of the mixture from the third step are present; fifth, mixing the mixtures from the first and fourth steps at high speed until homogenous; and sixth, mixing the mixtures from the second and fifth steps at high speed until homogenous. Those skilled in the art will appreciate how this formulation(s) may be scaled up or down to accommodate different batch sizes.

3. The Serum

The serum may comprise: organic aloe vera juice; xanthan gum; organic whole leaf wheat grass; carbamide peroxide; sweet almond oil; pure peppermint oil; and certified organic vegetable glycerin. A first embodiment of the disclosed composition may comprise the component ingredients in the following amounts: 40.00 grams of organic aloe vera juice; 3.00 grams of xanthan gum; 4.00 grams of wheat grass powder; 26.00 grams of carbamide peroxide; 6.00 grams of sweet almond oil; 2.00 grams of peppermint oil; and 100.00 grams of vegetable glycerin. A second embodiment of the disclosed composition may comprise the component ingredients in the following amounts: 40.00 grams of aloe vera juice; 3.00 grams of xanthan gum; 4.00 grams of wheat grass powder; 26.00 grams of carbamide peroxide; 12.00 grams of sweet almond oil; 2.00 grams of peppermint oil; and 100.00 grams of vegetable glycerin. A third embodiment of the disclosed composition may comprise the component ingredients in the following amounts: 40.00 grams of aloe vera juice; 3.00 grams of xanthan gum; 4.00 grams of wheat grass powder; 13.00 grams of carbamide peroxide; 12.00 grams of sweet almond oil; 2.00 grams of peppermint oil; and 100.00 grams of vegetable glycerin. A fourth embodiment of the disclosed composition may comprise the component ingredients in the following amounts: 40.00 grams of Organic aloe vera juice; 2.00 grams of xanthan gum; 4.00 grams of wheat grass powder; 26.00 grams of carbamide peroxide; 6.00 grams of sweet almond oil; 2.00 grams of peppermint oil; and 100.00 grams of vegetable glycerin. A fifth embodiment of the disclosed composition may comprise the component ingredients in the following amounts: 40.00 grams of aloe vera juice; 2.00 grams of xanthan gum; 4.00 grams of wheat grass powder; 26.00 grams of carbamide peroxide; 12.00 grams of sweet almond oil; 2.00 grams of peppermint oil; and 100.00 grams of vegetable glycerin. A sixth embodiment of the disclosed composition may comprise the component ingredients in the following amounts: 40.00 grams of aloe vera juice; 2.00 grams of xanthan gum; 4.00 grams of wheat grass powder; 13.00 grams of carbamide peroxide; 12.00 grams of Sweet Almond Oil; 2.00 grams of peppermint oil; and 100.00 grams of vegetable glycerin. The above recited preferable compositions are summarized by Table 4.

TABLE 4

| Compositions for the serum | | |
|---|---|---|
| Ingredient | Amount | |
| Serum #1 | | |
| aloe vera juice | 40.00 | gm |
| xanthan gum | 3.00 | gm |
| wheat grass | 4.00 | gm |
| carbamide peroxide | 26.00 | gm |
| sweet almond oil | 6.00 | gm |
| peppermint oil | 2.00 | gm |
| vegetable glycerin | 100.00 | gm |
| Serum #2 | | |
| aloe vera juice | 40.00 | gm |
| xanthan gum | 3.00 | gm |
| wheat grass | 4.00 | gm |
| carbamide peroxide | 26.00 | gm |
| sweet almond oil | 12.00 | gm |
| peppermint oil | 2.00 | gm |
| vegetable glycerin | 100.00 | gm |
| Serum #3 | | |
| aloe vera juice | 40.00 | gm |
| xanthan gum | 3.00 | gm |
| wheat grass | 4.00 | gm |
| carbamide peroxide | 13.00 | gm |
| sweet almond oil | 12.00 | gm |
| peppermint oil | 2.00 | gm |
| vegetable glycerin | 100.00 | gm |
| Serum #4 | | |
| aloe vera juice | 40.00 | gm |
| xanthan gum | 2.00 | gm |
| wheat grass | 4.00 | gm |
| carbamide peroxide | 26.00 | gm |
| sweet almond oil | 6.00 | gm |
| peppermint oil | 2.00 | gm |
| vegetable glycerin | 100.00 | gm |
| Serum #5 | | |
| aloe vera juice | 40.00 | gm |
| xanthan gum | 2.00 | gm |
| wheat grass | 4.00 | gm |
| carbamide peroxide | 26.00 | gm |
| sweet almond oil | 12.00 | gm |
| peppermint oil | 2.00 | gm |
| vegetable glycerin | 100.00 | gm |
| Serum #6 | | |
| aloe vera juice | 40.00 | gm |

TABLE 4-continued

Compositions for the serum

| Ingredient | Amount | |
|---|---|---|
| xanthan gum | 2.00 | gm |
| wheat grass | 4.00 | gm |
| carbamide peroxide | 13.00 | gm |
| sweet almond oil | 12.00 | gm |
| peppermint oil | 2.00 | gm |
| vegetable glycerin | 100.00 | gm |

181.00 grams of the first embodiment of the serum may preferably be prepared by: first, mixing 4.00 grams of aloe vera juice with 4.00 grams of wheat grass until the wheat grass powder is thoroughly hydrated; second, slowly mixing 3.00 grams of the xanthan gum with 16.00 grams of the aloe vera juice until no clumps of xanthan gum are present (which preferably should be allowed to thicken for a period of one to two hours); third, mixing 20.00 grams of aloe vera juice with 26.00 grams of carbamide peroxide until the carbamide peroxide is thoroughly dissolved; fourth, mixing 100.00 grams of vegetable glycerin, 6.00 grams of sweet almond oil, and 3.00 grams of peppermint oil; fifth, mixing the resultant mixtures of the first and fourth steps; sixth, mixing the resultant mixtures from the third and fifth step; and seventh, mixing the resultant mixtures from the second and sixth steps at high speed until the composition is homogenous.

187.00 grams of the second embodiment of the serum may preferably be prepared by: first, mixing 4.00 grams of aloe vera juice with 4.00 grams of wheat grass until the wheat grass powder is thoroughly hydrated; second, slowly mixing 3.00 grams of the xanthan gum with 16.00 grams of the aloe vera juice until no clumps of xanthan gum are present (which preferably should be allowed to thicken for a period of one to two hours); third, mixing 20.00 grams of aloe vera juice with 26.00 grams of carbamide peroxide until the carbamide peroxide is thoroughly dissolved; fourth, mixing 100.00 grams of vegetable glycerin, 12.00 grams of sweet almond oil, and 2.00 grams of peppermint oil; fifth, mixing the resultant mixtures of the first and fourth steps; sixth, mixing the resultant mixtures from the third and fifth step; and seventh, mixing the resultant mixtures from the second and sixth steps at high speed until the composition is homogenous.

174.00 grams of the third embodiment of the serum may preferably be prepared by: first, mixing 4.00 grams of aloe vera juice with 4.00 grams of wheat grass until the wheat grass powder is thoroughly hydrated; second, slowly mixing 3.00 grams of the xanthan gum with 16.00 grams of the aloe vera juice until no clumps of xanthan gum are present (which preferably should be allowed to thicken for a period of one to two hours); third, mixing 20.00 grams of aloe vera juice with 13.00 grams of carbamide peroxide until the carbamide peroxide is thoroughly dissolved; fourth, mixing 100.00 grams of vegetable glycerin, 12.00 grams of sweet almond oil, and 2.00 grams of peppermint oil; fifth, mixing the resultant mixtures of the first and fourth steps; sixth, mixing the resultant mixtures from the third and fifth step; and seventh, mixing the resultant mixtures from the second and sixth steps at high speed until the composition is homogenous.

180.00 grams of the fourth embodiment of the serum may preferably be prepared by: first, mixing 4.00 grams of aloe vera juice with 4.00 grams of wheat grass until the wheat grass powder is thoroughly hydrated; second, slowly mixing 2.00 grams of the xanthan gum with 16.00 grams of the aloe vera juice until no clumps of xanthan gum are present (which preferably should be allowed to thicken for a period of one to two hours); third, mixing 20.00 grams of aloe vera juice with 26.00 grams of carbamide peroxide until the carbamide peroxide is thoroughly dissolved; fourth, mixing 100.00 grams of vegetable glycerin, 6.00 grams of sweet almond oil, and 2.00 grams of peppermint oil; fifth, mixing the resultant mixtures of the first and fourth steps; sixth, mixing the resultant mixtures from the third and fifth step; and seventh, mixing the resultant mixtures from the second and sixth steps at high speed until the composition is homogenous.

186.00 grams of the fifth embodiment of the serum may preferably be prepared by: first, mixing 4.00 grams of aloe vera juice with 4.00 grams of wheat grass until the wheat grass powder is thoroughly hydrated; second, slowly mixing 2.00 grams of the xanthan gum with 16.00 grams of the aloe vera juice until no clumps of xanthan gum are present (which preferably should be allowed to thicken for a period of one to two hours); third, mixing 20.00 grams of aloe vera juice with 26.00 grams of carbamide peroxide until the carbamide peroxide is thoroughly dissolved; fourth, mixing 100.00 grams of vegetable glycerin, 12.00 grams of sweet almond oil, and 2.00 grams of peppermint oil; fifth, mixing the resultant mixtures of the first and fourth steps; sixth, mixing the resultant mixtures from the third and fifth step; and seventh, mixing the resultant mixtures from the second and sixth steps at high speed until the composition is homogenous.

173.00 grams of the sixth embodiment of the serum may preferably be prepared by: first, mixing 4.00 grams of aloe vera juice with 4.00 grams of wheat grass until the wheat grass powder is thoroughly hydrated; second, slowly mixing 2.00 grams of the xanthan gum with 16.00 grams of the aloe vera juice until no clumps of xanthan gum are present (which preferably should be allowed to thicken for a period of one to two hours); third, mixing 20.00 grams of aloe vera juice with 13.00 grams of carbamide peroxide until the carbamide peroxide is thoroughly dissolved; fourth, mixing 100.00 grams of vegetable glycerin, 12.00 grams of sweet almond oil, and 2.00 grams of peppermint oil; fifth, mixing the resultant mixtures of the first and fourth steps; sixth, mixing the resultant mixtures from the third and fifth step; and seventh, mixing the resultant mixtures from the second and sixth steps at high speed until the composition is homogenous.

B. Related Methods of Use

The disclosed compositions are suitably nutrient rich and beneficial to oral health and wellness. Suitably, the disclosed composition is non-toxic and may be used to promote oral health and wellness, protect the body, and strengthen the immune system. Additionally, the disclosed compositions are nutrient rich whereby application of the composition to components of the oral cavity results in the delivery of nutrients to the oral cavity via absorption. For example, wheat grass possesses antioxidants, 13 of the 16 amino acids (including all 8 of the essential amino acids), vitamins (A, B1, B2, B3, B5, B6, B8, B12, C, E, and K), Superoxide Dismutase (SOD), P4D1, Muco-polysacharides, and Chlorophyll which are readily absorbed by the soft tissues of an oral cavity when contacted by the disclosed composition. For another example, Sweet almond oil is rich in unsaturated fat and essential fatty acids, and Omega-3, which nutrients are readily absorbable by soft tissue. For yet another example, Additionally, the disclosed composition is rejuvinative because mineral ions within the ingredients of the composition may be taken up by saliva (a combination of the water from the saliva and the carbon dioxide from breath, i.e., carbonic acids) and restored to the teeth. Said remineralization reduces tooth sensitivity and increases enamel strength. Further, ingredients, e.g., Aloe Vera Juice or powder, within the compositions possess antiseptic agents (including: lupeol, salicylic acid, urea nitrogen, cinnomonic acid, phenols, and sulfur), treat infections, help cure wounds, and inhibit the growth of fungi, *Streptococcus*, and *Shigella*, and help reduce gingivitis, plaque, and tartar build-up. Further still, the ingredients, including sweet almond oil, strengthen the immune system and possess anti-inflammatory attributes. Finally, the composition can be used to treat dry mouth (Xerostomia) because: Sweet Almond Oil provides lubricating emollients to dry tissues; Pure Peppermint Oil gives a cooling effect to dry tissues; Vegetable Glycerin has excellent moisturizing properties which aid in retaining moisture; and, Xylitol stimulates saliva glands thereby increasing saliva in the mouth.

In use, the rinse composition may be applied to the inner components of the oral cavity. More specifically, the composition may be swished in the mouth before discarding the used composition.

As an alternative use, the rinse composition may be placed in a dispenser similar to U.S. Pat. No. 4,023,712 (issued May 17, 1977) (this and other known dispensers are hereby incorporated by reference and fully set forth herein) for sprayed application to the inner components of the oral cavity. Suitably, dry mouth (Xerostomia) may be treated by spraying certain embodiments of the rinse composition into the mouth so that the affected tissue is coated, moisturized, soothed, and/or healed. The various embodiments of the composition may further: deliver nutrients to the soft tissues of the oral cavity; treat wounds; kill pathogens and halitosis causing bacteria/fungus; and, clean, strengthen and whiten the teeth.

In use, the oral care gel or toothpaste may be applied to the inner components of the oral cavity. However, a preferable manner and system of application of the compositions for oral health care vary. In a preferable manner of application, the oral care gel or tooth paste may be applied topically to the internal components of the oral cavity via a pen or brush dispenser similar to dispensers disclosed by U.S. Pat. No. 6,474,891 (issued Nov. 5, 2002) and U.S. Pat. No. 7,309,185 (issued Dec. 18, 2007) (these and other known dispensers are hereby incorporated by reference and fully set forth herein). More specifically, the toothpaste may be placed inside the reservoir of a dispensing pen or brush and thereby topically applied to the inner components of the oral cavity without brushing or rinsing. In another preferable manner of use, the gel composition may be used to treat dry mouth (Xerostomia) via the application of the composition to the affected oral tissue by either: (a) placing the composition on a finger and spreading the composition over the affected tissue; or (b) placing the gel in a tube and directing the substance from the tube to an affected area. Suitably, the applied gel composition coats, moisturizes, soothes, and/or promotes growth and healing of the affected tissue.

The composition may: deliver nutrients to the soft tissues of the oral cavity; treat wounds; kill pathogens and halitosis causing bacteria/fungus; and, clean, strengthen and whiten the teeth.

Alternatively, the toothpaste may be used in the ordinary manner of toothpaste. More specifically, the composition may be placed on the bristles of a toothbrush and thereby applied to the teeth, gums, tongue, and other soft-tissues of the oral cavity before rinsing the used oral care gel with the rinse composition. The composition may: deliver nutrients to the soft tissues of the oral cavity; treat wounds; kill harmful pathogens and halitosis causing bacteria/fungus; and, clean, strengthen and whiten the teeth.

It should be noted that the healing properties of the toothpaste are not limited to oral applications. That is to say, the toothpaste may also be used to treat cuts or scraps. More specifically, the toothpaste may be placed inside the reservoir of a dispensing pen or brush and thereby topically applied to cuts or scrapes outside of the oral cavity to assist in wound treatment.

To combat the constant growth and contamination of bacteria, periodic delivery of toxic loads, and general degradation of oral health that occur throughout a day, this application further discloses a system for facilitating good oral health. Preferably, the system comprises: an amount (e.g., four ounces (4 oz)) of the toothpaste for use as a Brushing Gel or toothpaste; a tooth brush; an amount (e.g., sixteen ounces (16 oz)) of the mouth rinse; an amount (e.g., two milliliters (2 ml)) of the oral care gel disposed within the reservoir of a dispensing pen or brush; and an amount (e.g., one ounce (1 oz)) of the rinse composition disposed within a spray dispenser. Preferable daily use of the system may consist essentially of the following steps: (1) placing approximately one-fourth of a teaspoon of the toothpaste onto the bristles of the toothbrush and, using circular motions, cleaning the teeth, gums, tongue and other soft tissues of the mouth using the gel-plus-bristles; (2) rinsing the oral cavity of the toothpaste residue by placing approximately one-fourth ounce of the mouth rinse into the oral cavity and swishing it therein for at least sixty seconds (60 sec); (3) topically applying, without brushing or rinsing, the toothpaste gel to the teeth, gums, tongue, and soft tissues of the mouth via the dispensing pen or brush; (4) spraying the mouth spray onto the inner components of the oral cavity via the spray dispenser; (5) repeating step (3) and/or (4) periodically throughout the day; and, (6) completing steps (1) and (2) at least once more.

The serum may suitably be used for antimicrobial activity against *Candida albicans, Porphyromonas gingivalis, Prevotella intermedia, Fusobacterium nucleatum, Campylobacter rectus, Actinobacillus actinomycetemcomitans* (reclassified as *Aggregatibacter actinomycetemomitans* (Aa)) and *Streptococcus mutans*. In one instance: (1) fresh (24 hour broth) cultures of *Candida albicans, Porphyromonas gingivalis, Prevotella intermedia, Fusobacterium nucleatum, Campylobacter rectus, Aggregatibacter actinomycetemomitans* (Aa) and *Streptococcus mutans* were individually swabbed onto blood agar plates to provide a confluent lawn of microbial growth; (2) the inoculums were allowed to absorb into their respective agar host for 5 minutes; (3) specimens of each serum composition was aseptically pipetted (5 ul) onto designated places on the plates and allowed to adsorb (or adhere, in the case of the undiluted sera) into the agar; (4) the plates were incubated, agar-side up, at 37 deg. Celsius in GasPak anaerobic jars or in %5 CO sub. 2 for seventy two hours; the plates were examined for zones of inhibition, wherein the diameter of each zone of inhibition was between 9 and 50 millimeters (the zone of inhibition for a chlorhexidine (0.12%) control was between 10 and 40 millimeters).

The serum may also be used with root planing, routing prophylaxis, periodontal scaling, gingival curettage, core retention techniques, extractions, and operative or post operative procedures. In a preferable mode of use, the serum may be used to fight pathogens that have infected the periodontal pocket (defined as the area located four or more millimeters below the gum-line between two teeth). In said preferred mode of use, the serum may be loaded into a syringe and injected, via an irrigation needle, into the periodontal pocket. In one instance, the serum may be injected into a periodontal pocket that is 12 to 13 millimeters below the gum line. Suitably, the viscosity of the serum allows the serum to remain in the periodontal pocket without being rejected by the natural processes of the human body. In another instance, the serum may be placed on wounds (e.g., in the socket of a tooth extraction) to promote tissue growth and fight bacterial infection.

It should be noted that the above description and recited embodiments or examples are of illustrative importance only. In other words, the descriptions of the present disclosure should not be construed as limiting of the subject matter in this application. Additional modifications may become apparent to one skilled in the art after reading this disclosure.

We claim:

1. A composition for oral health care comprising:
2,395 grams of xylitol;
119.7 grams of peppermint oil;
981.9 grams of vegetable glycerine;
910.1 grams of aloe vera juice;
718.5 grams of carbamide peroxide;
311.3 grams of sweet almond oil;
119.7 grams of wheat grass powder;
12.9 grams of xanthan gum; and
5.98 gallons of water.

2. The composition of claim 1, wherein the composition is formulated in a rinse.

3. The composition of claim 2, wherein the rinse is for use in children.

4. A composition for oral health care comprising:
554 grams xylitol;
4 grams peppermint oil;
168 grams vegetable glycerine;
0.5 grams aloe vera powder;
100 grams carbamide peroxide;
44 grams of sweet almond oil;
4 grams wheat grass powder; and
8 grams xanthan gum.

5. The composition of claim 4, wherein the composition is formulated into a gel.

* * * * *